(12) United States Patent
Guillermo

(10) Patent No.: US 8,551,054 B2
(45) Date of Patent: Oct. 8, 2013

(54) DEVICE FOR A MEDICAMENT DELIVERY DEVICE

(75) Inventor: Carlos Guillermo, Los Osos, CA (US)

(73) Assignee: SHL Group AB, Nacka Strand (SE)

( * ) Notice: Subject to any disclaimer, the term of this patent is extended or adjusted under 35 U.S.C. 154(b) by 561 days.

(21) Appl. No.: 12/993,523

(22) PCT Filed: May 5, 2009

(86) PCT No.: PCT/EP2009/055385
§ 371 (c)(1),
(2), (4) Date: Nov. 19, 2010

(87) PCT Pub. No.: WO2009/141219
PCT Pub. Date: Nov. 26, 2009

(65) Prior Publication Data
US 2011/0071477 A1    Mar. 24, 2011

(30) Foreign Application Priority Data
May 20, 2008    (SE) ...................................... 0801166

(51) Int. Cl.
*A61M 5/315*    (2006.01)
(52) U.S. Cl.
USPC .......................................... 604/218; 604/230
(58) Field of Classification Search
USPC ......... 604/181, 187, 218, 219, 220, 221, 225, 604/226, 228, 230
See application file for complete search history.

(56) References Cited

U.S. PATENT DOCUMENTS

| | | | | |
|---|---|---|---|---|
| 4,632,672 A | * | 12/1986 | Kvitrud | 604/222 |
| 5,300,030 A | * | 4/1994 | Crossman et al. | 604/136 |
| 6,090,078 A | * | 7/2000 | Erskine | 604/198 |
| 8,277,414 B2 | * | 10/2012 | Barrow-Williams et al. | 604/136 |
| 8,313,465 B2 | * | 11/2012 | Harrison | 604/136 |
| 2004/0024367 A1 | | 2/2004 | Gilbert | |

FOREIGN PATENT DOCUMENTS

| | | |
|---|---|---|
| EP | 1795218 A1 | 6/2007 |
| GB | 2414404 A * | 5/2004 |
| WO | 00/24441 A1 | 10/1998 |
| WO | 03/097133 A1 | 11/2003 |
| WO | WO/03/097133 A1 * | 11/2003 |

OTHER PUBLICATIONS

EPO, Int'l Search Report in PCT/EP2009/055385, Nov. 4, 2009.
EPO, Written Opinion in PCT/EP2009/055385, Nov. 4, 2009.

* cited by examiner

*Primary Examiner* — Kevin C Sirmons
*Assistant Examiner* — Andrew Gilbert
(74) *Attorney, Agent, or Firm* — Potomac Patent Group PLLC

(57) ABSTRACT

The present invention relates to damper for a medicament delivery device, which device comprises a container containing medicament, a stopper arranged in said container and movable for expelling said medicament through a dose delivery means, a plunger rod having opposing proximal and distal ends and capable of acting on said stopper, and force means capable of exerting a force on said plunger rod, wherein said damper comprises a tubular sleeve having opposing proximal and distal ends; said sleeve comprises a compartment formed by a closed end wall at the proximal end of the sleeve and the proximal end of the plunger rod which is positioned in an open end at the distal end of the sleeve; and wherein said compartment comprises a sealable and resilient pad, a fluid, and at least one passage for expelling said fluid in an annular space between said sleeve and an inner wall of said container, thereby creating a dampening force, upon movement of said plunger rod.

4 Claims, 3 Drawing Sheets

DEVICE FOR A MEDICAMENT DELIVERY DEVICE

TECHNICAL FIELD

The present invention relates to a device for a medicament delivery device and in particular a damping device capable of dampening the force from a plunger rod acting on a stopper of a container arranged in said medicament delivery device.

BACKGROUND ART

Medicament delivery devices as e.g. injectors for injecting medicament into the tissue of patients have become widely used, and in particular since these injectors have facilitated for larger groups of patients to self-administer their drugs, due to the functionalities of the injectors.

Examples of functionalities of the injectors are auto-penetration and/or auto-injection. A common design for auto-injection that could also be used for the preceding penetration is to have a loaded compression spiral spring acting on a plunger rod, which in turn is acting on a stopper arranged in a medicament cartridge or syringe. When the spring is released, a high force will be acting on the plunger rod and thus the stopper and the body of the syringe. Often the spring is at very high tension, particularly at the beginning of its stroke, why forces applied may be considerable. It is not uncommon that the stopper has adhered to the inner wall of the cartridge or syringe, for example due to the material properties of the stopper and long time storage. In order to handle this, the spring has to be dimensioned such that it has the necessary force to release the stopper.

This in turn, a well as the sudden impact of the plunger rod on the stopper, increases the risk of breaking the cartridge or syringe that often is made of glass. This situation has to be avoided, because if it occurs, the patient may not be able to receive any medication, which might be fatal.

One solution to this problem is disclosed in WO 00/24441 describing an auto-injector arranged with penetration/injection dampening means. According to one embodiment the damper comprises a stator part attached to the injector head (plunger rod) and a toothed rotor wheel engaging a toothed rail. During movement of the injector head the rotor wheel is also moved, and a retarding force is obtained between the rotor wheel and the rail.

According to another embodiment, the damper is a viscous damper with a piston arranged in a cylinder in the injector head. During movement oil in the cylinder passes flow restrictions in the piston, thereby creating a dampening action.

However, both embodiments disclosed in WO 00/24441 are not very feasible. The rotational damper is rather bulky and comprises many components. The viscous damper requires seals so that the oil cannot escape into the injector, which could be a problem when storing the injector for longer periods. Also, many types of oils are not compatible with many types of polymers, thereby risking degeneration of the components of the injector.

Document GB 2 414 404 discloses an injector arranged with a dampening means comprising a compartment in a second part of a plunger rod comprising highly viscous fluid and a first part of the plunger rod releasably attached to the second part. When the plunger rod has moved a certain distance during penetration and injection, the first part is released and then acts on the fluid in the compartment, whereby the fluid is forced through a vent bore, dampening the movement of the first part relative the second part. The aim for this is to delay the release of the syringe to allow remaining content of the syringe to be discharged before syringe is released. The delay is used to compensate for any stacking of tolerances in the injector.

Document WO 031097133 intends to solve the same problem as GB 2 414 404, but instead of a viscous fluid, a compartment in the front part of a plunger rod contains air, which air is pressed through a small aperture by a second part of the plunger rod acting on the compartment.

None of the documents GB 2 414 404 or WO 031097133 really disclose a dampening function but rather a delay function ensuring that an injection is completed before the needle is automatically withdrawn from the injection site.

BRIEF DESCRIPTION OF THE INVENTION

It is an object of the present invention to remedy the problems of the state of the art and to provide a suitable damping means that does not take up additional space nor affect the components of the medicament delivery device during storage.

The object is obtained with a medicament delivery device according to the features of independent claim 1. Preferable embodiments of the invention form the subject of the dependent patent claims.

According to a main aspect of the invention it is characterised by a damper for a medicament delivery device, which device comprises a medicament container comprising a proximal opening with or for receiving a dose delivery means, an axially movable stopper, and an enclosure containing medicament; a plunger rod having opposing proximal and distal ends; and force means operably connected to said plunger rod for exerting a force on said plunger rod such that said plunger is moved within said container; wherein said damper comprises a tubular sleeve having opposing proximal and distal ends; said sleeve comprises a compartment formed by a closed end wall at the proximal end of the sleeve and the proximal end of the plunger rod which is positioned in an open end at the distal end of the sleeve; and wherein said compartment comprises a sealable and resilient pad, a fluid, and at least one passage for expelling said fluid in an annular space between said sleeve and an inner wall of said container, thereby creating a dampening force, upon movement of said plunger rod.

According to another aspect of the invention, said resilient pad is arranged and designed to cover said at least one passage when said resilient pad is in a released position.

According to a further aspect of the invention, said fluid is arranged between an impermeable surface of said resilient pad and the proximal end of the plunger rod, such that said fluid is capable of being expelled through said at least one passage when said resilient pad is compressed and thereby freeing said at least one passage due to a force applied on said compartment by said plunger rod.

According to yet an aspect of the invention, at least one groove having a predetermined length is axially extending on the outer circumference surface of the plunger rod forming at least one passage between the distal inner circumferential surface of the sleeve and the proximal outer circumferential surface of the plunger rod for leading any air entrapped inside the compartment.

There are a number of advantages with the present invention. Due to that the at least one passage is covered before the compartment is exposed to pressure and that the fluid may be a liquid with high viscosity and is arranged between the moving plunger rod and the resilient pad, the liquid will act as a hydraulic damper due to the shear force in the viscous liquid.

These and other aspects of and advantages with the present invention will become apparent from the following detailed description and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
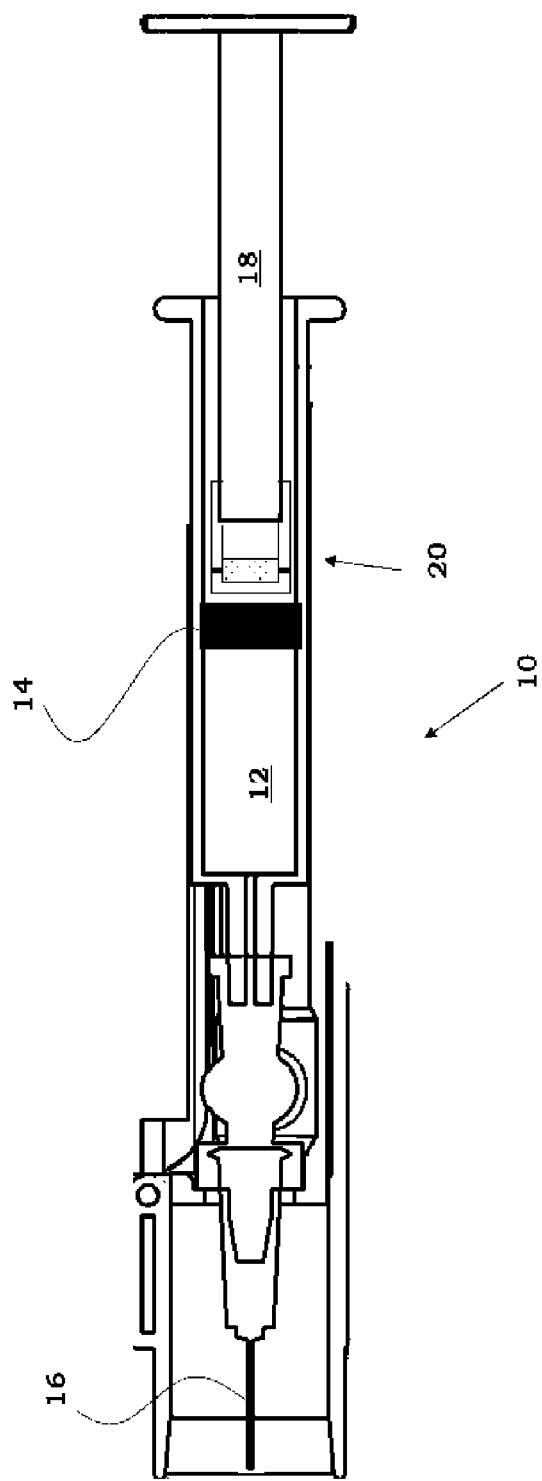
FIG. 1 is a detailed view in cross-section of an injector comprising the present invention.

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the injection device is located closest to the medicament delivery site of the patient. The present invention is to be used in a medicament delivery device comprising a medicament container 12, a plunger rod 18 having opposing proximal and distal ends, and force means operably connected to said plunger rod for exerting a force on said plunger rod such that said plunger is moved within said container. The medicament container comprises a proximal opening with or for receiving a dose delivery means 16 means as e.g. an injection needle, an aerosol nozzle, a nebulising nozzle, a spray nozzle; an axially movable stopper 14, and an enclosure containing medicament. In FIG. 1, a medicament delivery device, as in e.g. an injector 10, is schematically shown. Said injector comprises: a container 12 arranged with a stopper 14 movable inside said container for expelling medicament through a dose delivery means 16 attached to the container when the stopper is moved by a plunger rod 18. In FIG. 1 the container 12 is shown as a syringe and the dose delivery means is shown as a needle 16.

The plunger rod is connected to a power pack (not shown) that may comprise a force means as e.g. a compression spiral spring, a torque spring or the like that is held in a loaded state or that may be loaded to a loaded state. When the resilient force means is released from its loaded state, the plunger rod is displaced towards the proximal end of the medicament delivery device and thus the stopper is also displaced towards the proximal end of the medicament delivery device for expelling medicament through the dose delivery means.

At the proximal end of the plunger rod, a damper 20 according to the present invention is arranged. In the embodiment shown in FIG. 2, it comprises a tubular sleeve 22 having opposing proximal and distal ends. Said sleeve comprises a compartment formed by a closed end wall at the proximal end of the sleeve and the proximal end of the plunger rod which is positioned in an open end at the distal end of the sleeve. The sleeve also comprises an inner diameter that is somewhat smaller than the outer diameter of the plunger rod and an outer diameter that is somewhat smaller than the inner diameter of the container. The compartment comprises a sealable and resilient pad, a fluid 24, and at least one passage 26 for expelling said fluid in an annular space 32 between said sleeve and an inner wall of said container, thereby creating a dampening force, upon movement of said plunger rod.

Figure 2:
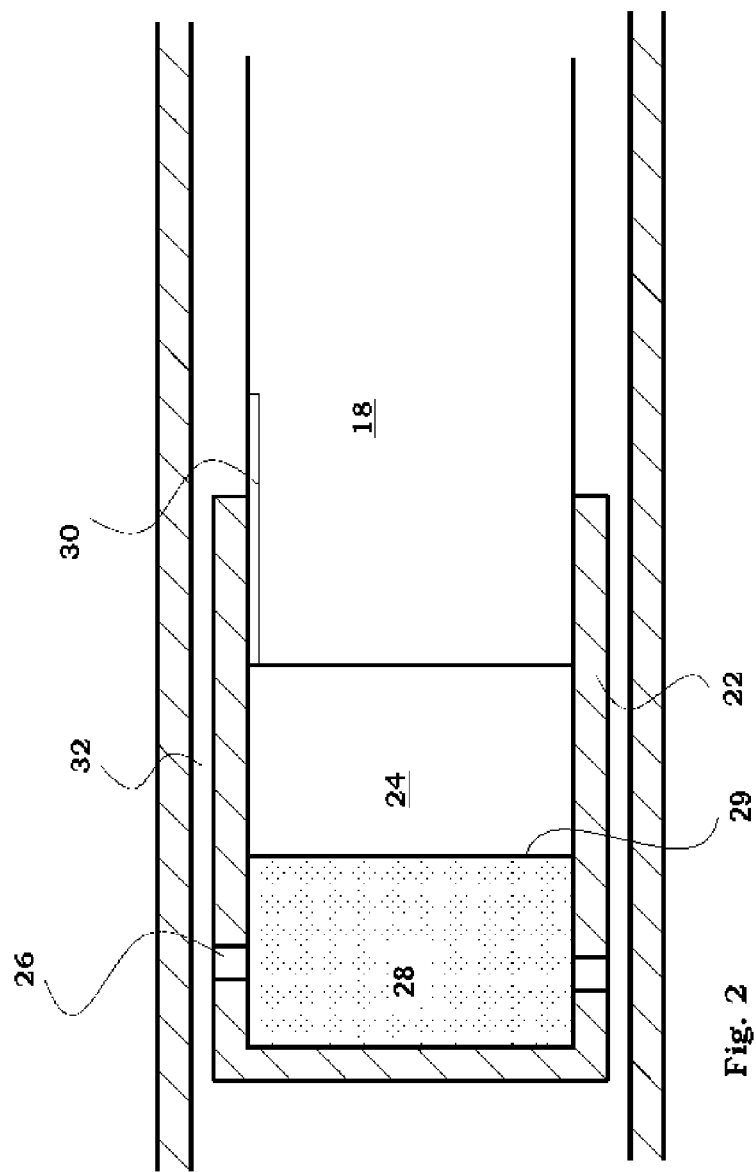
FIG. 2 is a part view of an embodiment of a damper according to the present invention unaffected.
Figure 3:
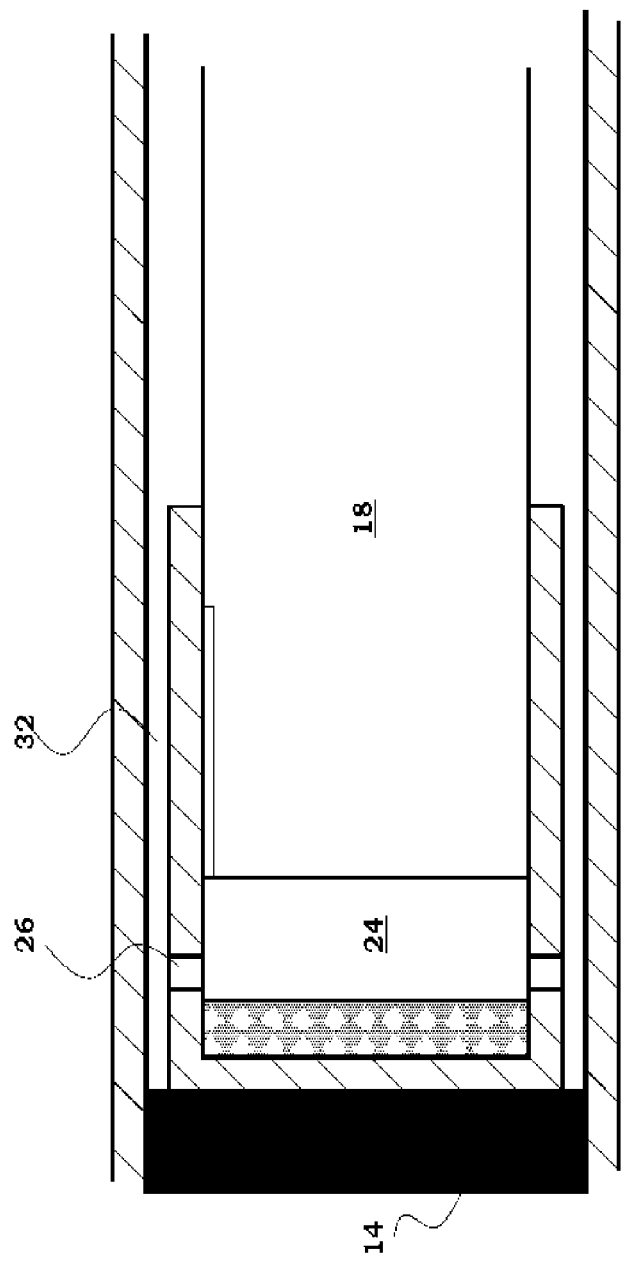
FIG. 3 is the view of FIG. 2 when the damper is being affected.

The at least one passage 26 is arranged at a predetermined distance from the closed end wall and around the circumferential surface of the sleeve. The sealable and resilient pad 28 is arranged adjacent the closed end wall at the proximal end of the sleeve and comprises a resilient material and an impermeable surface 29, as will be explained below. The pad covers the at least one passage when it is adapted in a released position, as seen in FIG. 2. The rest of the compartment is filled with the fluid 24 e.g. a liquid with rather high viscosity, such as silicone grease, a gel or the like. At the proximal end of the plunger rod, at least one groove 30 having a predetermined length is axially extending on the outer circumference surface of the plunger rod forming at least one passage between the distal inner circumferential surface of the sleeve and the proximal outer circumferential surface of the plunger rod. The annular space 32 may also comprises small channels created by a ribbed outer surface of the sleeve.

The damper according to the present invention is intended to function as follows. The closed end wall of the damper abuts the stopper 14. When a force is applied on the plunger rod 18 for delivering medicament, it is moved towards the proximal end of the medicament delivery device with a high force. The stopper also starts to move towards the proximal end of the medicament delivery device as the proximal end of the plunger rod slides into the compartment. This causes a pressure build-up in the fluid inside the compartment, which in turn causes a compression of the resilient pad 28. Any air entrapped inside the compartment will be forced out through the at least one groove 30.

When the resilient pad 28 has been compressed to a certain extent the at least one passage 26 are freed, whereby the fluid is forced through said at least one passage out into the annular space 32. Because of the high viscosity and other suitable properties of the fluid, it will provide a dampening effect on the plunger rod as it moves because of the shear forces in the fluid. In this aspect, the size of the compartment is preferably chosen such that it corresponds to the size of the annular gap.

It is to be understood that the embodiment described above and shown in the drawings is to be regarded as a non-limiting example of the present invention and that it may be modified in many ways within the scope of the patent claims.

The invention claimed is:

1. A damper for a medicament delivery device that includes a container containing medicament, a stopper arranged in the container and movable for expelling the medicament through a dose delivery device, a plunger rod acting on the stopper, and a force device configured for exerting a force on the plunger rod, the damper comprising:
   a tubular sleeve having opposing proximal and distal ends and comprising a compartment formed by a closed end wall at the proximal end of the tubular sleeve and a proximal end of the plunger rod which is positioned in an open end at the distal end of the tubular sleeve;
   a high-viscosity fluid arranged inside the compartment;
   at least one passage formed between the compartment and an annular space between the plunger rod and an inner wall of the container; and
   a resilient and sealable pad positioned in the compartment and arranged to cover the at least one passage when the resilient and sealable pad is in a released position, wherein when the force device is activated for exerting a force applied on the compartment by the plunger rod for expelling medicament, the resilient pad is compressed such that the at least one passage is freed, expelling the high-viscosity fluid into the annular space between the plunger rod and the inner wall of the container, thereby creating a dampening force.

2. The damper of claim 1, wherein at least one groove having a predetermined length axially extends on an outer circumference surface of the plunger rod forming at least one passage between a distal inner circumferential surface of the sleeve and a proximal outer circumferential surface of the plunger rod for allowing air entrapped inside the compartment to be expelled out through the at least one groove when a force is applied to the plunger rod.

3. The damper of claim 1, wherein the resilient and sealable pad comprises an impermeable surface arranged against the high-viscosity fluid.

4. The damper of claim 3, wherein at least one groove having a predetermined length axially extends on an outer circumference surface of the plunger rod forming at least one passage between a distal inner circumferential surface of the sleeve and a proximal outer circumferential surface of the plunger rod for allowing air entrapped inside the compartment to be expelled out through the at least one groove when a force is applied to the plunger rod.

* * * * *